United States Patent [19]
Carter et al.

[11] Patent Number: 5,674,264
[45] Date of Patent: Oct. 7, 1997

[54] FEEDBACK SYSTEM TO CONTROL ELECTRODE VOLTAGES IN A COCHLEAR STIMULATOR AND THE LIKE

[75] Inventors: Paul Carter, Carlingford; David Money, Pennant Hills, both of Australia

[73] Assignee: Cochlear Ltd., Lane Cove, Australia

[21] Appl. No.: 587,459

[22] Filed: Jan. 17, 1996

[30] Foreign Application Priority Data

Dec. 1, 1995 [WO] WIPO ............... PCT/AU95/00805

[51] Int. Cl.$^6$ .................................................. A61N 1/08
[52] U.S. Cl. ............................................. 607/57; 607/63
[58] Field of Search ................................. 607/13, 55–57, 607/63, 64, 68, 70

[56] References Cited

U.S. PATENT DOCUMENTS

| | | | |
|---|---|---|---|
| 4,343,312 | 8/1982 | Cals et al. ............................. | 607/13 |
| 4,408,608 | 10/1983 | Daly et al. ............................ | 607/57 |
| 4,858,610 | 8/1989 | Callaghan et al. ................... | 607/13 |
| 4,991,583 | 2/1991 | Silvian ................................. | 607/13 |
| 5,165,404 | 11/1992 | Andersson et al. .................. | 607/13 |

*Primary Examiner*—William E. Kamm
*Assistant Examiner*—George R. Evanisko
*Attorney, Agent, or Firm*—Gottlieb, Rackman & Reisman

[57] ABSTRACT

An implanted device such as cochlear implant having electrodes is provided with a pulse generator for generating stimulating pulses. The pulses are adjusted to insure that during the idle periods between the pulses, the voltage on the electrodes is at zero or at a preselected level. In one embodiment, the pulse durations or amplitudes adjusted, In another embodiment the voltage on the electrodes is measured before and during each pulse to determine IR drops from the electrodes to a reference point, and to compensate for the same.

9 Claims, 6 Drawing Sheets

FEEDBACK SYSTEM TO CONTROL ELECTRODE VOLTAGES IN A COCHLEAR STIMULATOR AND THE LIKE

BACKGROUND OF THE INVENTION

A. Field of Invention

This invention pertains to a cochlear implant systems using a plurality of electrodes to apply stimulation related, for example, to ambient sounds, to a patient's tissues or nerves and more particularly to a system adapted to reduce and/or control the voltages across the electrode/tissue interfaces when the electrodes are inactivate.

B. Description of the Prior Art

The subject invention pertains primarily to tissue stimulating systems. For example, electrode systems are known for providing therapy to a patient suffering loss of hearing. All of these systems typically require two sections: an internal or implanted section, and an external section. The external section includes a microphone for receiving ambient sounds and converting them into corresponding electrical signals. These electrical signals are processed and sent to the implanted section. The implanted section then generates stimulation signals used to excite the auditory nerve of the patient between an intra-cochlear electrode array and one or more extra-cochlear electrodes.

These electrodes are normally metallic and the interface impedance between the electrode and the tissue is largely capacitive. Therefore, when current is passed through these electrodes the voltage between the electrodes and the tissue (i.e., the electrode voltage) changes, as it does when current is passed through any capacitor. One disadvantage of this phenomenon is that the rate at which electrochemical reactions at the metal/tissue interface proceed is a function of the voltage across that interface. Reactions that at resting potential (i.e., the potential of the electrode metal with respect to the tissue with no applied current) are so slow as to be insignificant can become significant when the potential across the metal/tissue interface changes.

Manufacturers of cochlear implant systems therefore have to be careful to control electrode voltages to keep them in a region where any electrochemical reactions occur at a rate too slow to cause damage.

Different electrochemical reactions occur at different voltage levels and their rate is not a necessarily monotonic relationship with the electrode voltage. Therefore, careful control of the electrode voltages can minimize harmful electrochemical reactions resulting from stimulation.

One method normally used to control the electrode voltages consists of connecting all the electrodes together, through low impedance switches, (i.e., shorting the electrodes) after every stimulation pulse.

Another method consists of providing decoupling capacitors in series with the electrodes. However, these capacitors are bulky and take up valuable space in the implant.

Both methods described above are capable of maintaining a substantially minimal DC current between the electrodes during idle periods, however, they cannot be used to control the DC voltage level between the electrodes and the tissue.

OBJECTIVES AND SUMMARY OF THE INVENTION

In view of the above-mentioned disadvantages of the prior art, it is an objective of the present invention to provide a cochlear implant having, during idle periods, a preselected DC voltage between different stimulation electrodes or between the stimulating electrodes and the tissue.

A further objective is to provide a cochlear implant wherein stimulation pulses are applied by electrodes to a patient's aural nerve, said stimulation pulses being arranged to provide a preselected DC voltage between said electrodes during the idle periods between the pulses.

A further objective is to provide a cochlear implant with means for substantially eliminating DC electrode voltages between different electrodes during idle periods, if required.

Other objectives and advantages of the invention shall become apparent from the following description. Briefly, a cochlear implant system constructed in accordance with this invention includes a housing arranged and constructed for implantation subcutaneously into a patient, an electrode array coupled to said housing and extending into the cochlea for applying stimulation pulses to the patient's aural nerve, and means disposed in said housing for selectively controlling said pulses in a manner selected to result in a preselected voltage between said electrodes during idle periods between said pulses. The preselected voltage may be substantially zero or at a small level selected to minimize electrochemical reactions at the electrodes. Alternatively, the implant may be provided with a zero-crossing sensing network for obtaining said preselected voltage.

DETAILED DESCRIPTION OF THE INVENTION

Figure 1:
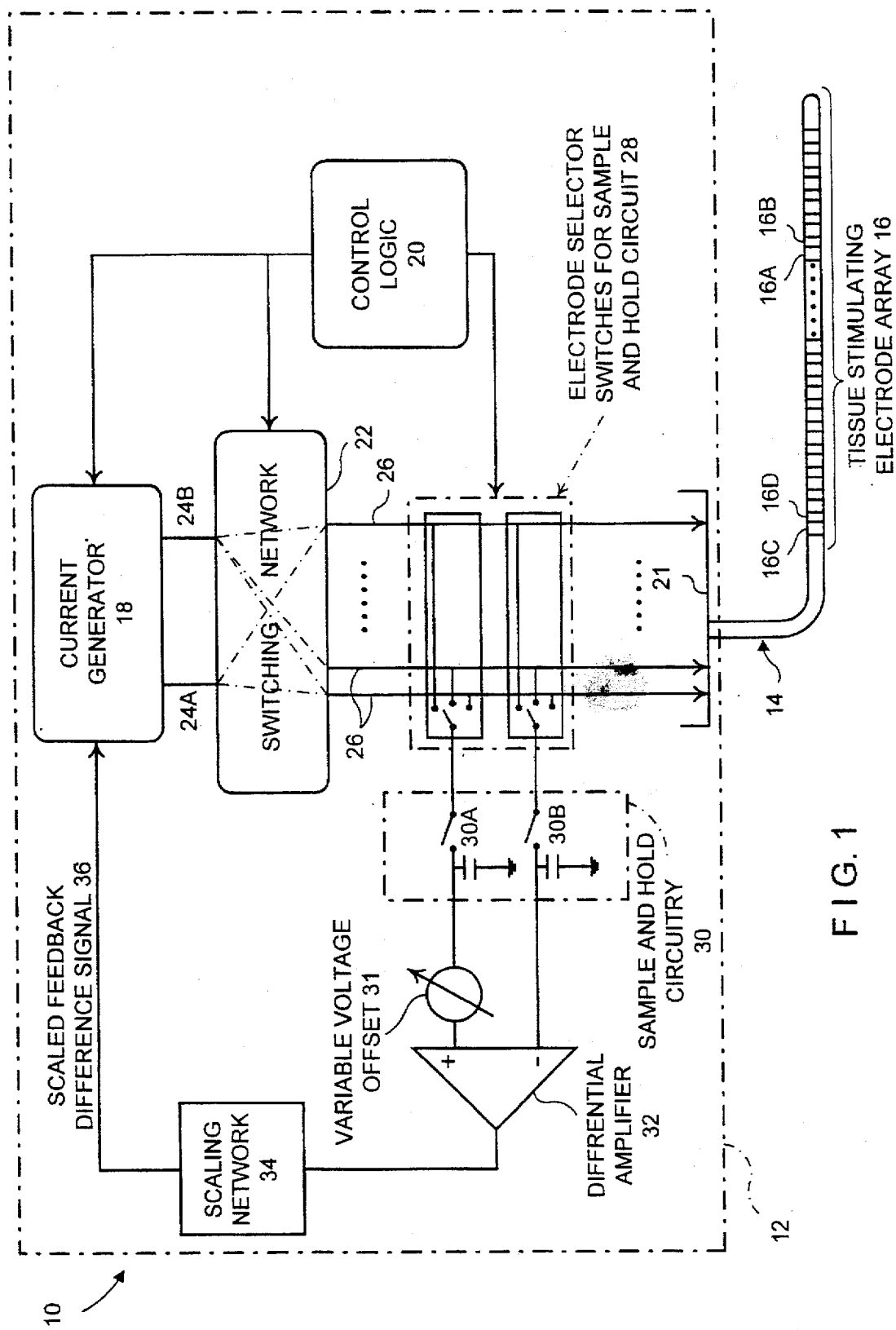
FIG. 1 shows a block diagram of a cochlear implant constructed in accordance with the present invention.
Figure 2:
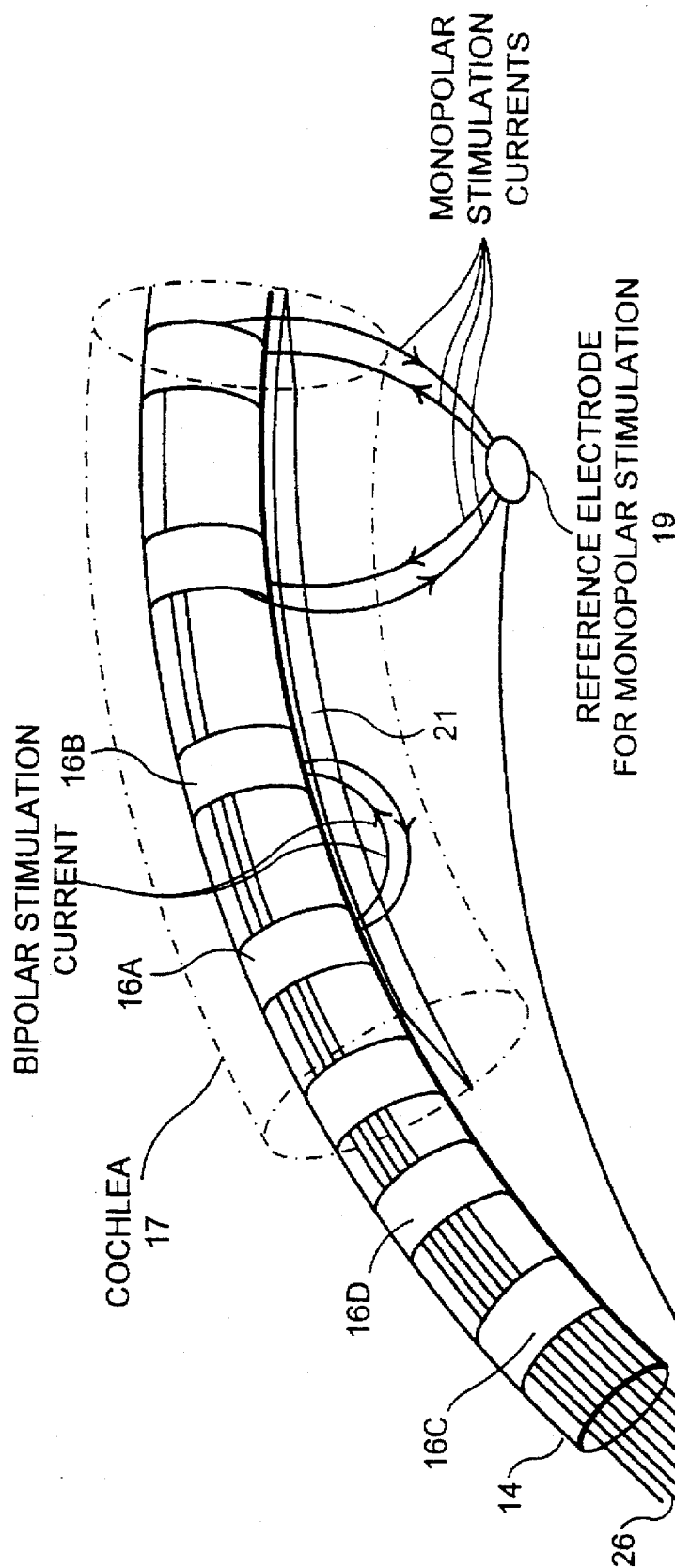
FIG. 2 shows a somewhat diagrammatic view of the electrode array used in the implant of FIG. 1.

Referring now to FIGS. 1 and 2, a cochlear implant 10 constructed in accordance with this invention includes an implantable housing 12 and an electrode carrier 14 terminating in an electrode array 16. Array 16 is preferably composed of two sets of electrodes: a set of inter-cochlear electrodes, such as electrodes 16A, 16B ... arranged and constructed to be disposed in the cochlea 17 of the patient and a set of extra-cochlear electrodes such as electrodes 16C, and 16D. More particularly, the intra-cochlear electrodes 16A, 16B ... of electrode array 16 are disposed adjacent to the basilar membrane 21 and the associated auditory nerve (not shown). Optionally, additional extra-electrodes 19 may be provided extending from the housing 12 or a portion of the housing 12 may be made conductive to form an extra-cochlear electrode (not shown).

Housing 12 includes various circuitry, such as a current generator 18, control logic 20, and a switching network 22. In response to external signals from a receiver (not shown), the control logic 20 sets the current generator to generate cochlear stimulation current pulses on lines 24A and 24B to switching network 22. The switching network 22, in response to control signals from logic 20 couples these cochlear stimulation signals sequentially to one of the electrodes of array 16 through conductors 26. Biphasic pulses are normally generated between the said electrodes.

Importantly, in accordance with this invention, the housing 10 further includes a plurality of electrode selector switches 28, a sample-and-hold (S/H) circuit 30, a variable voltage offset source 31, and a differential amplifier 32. The electrode switches 28 are used by the control logic 20 to connect two of the electrodes of array 16 (or any other electrodes present) via the appropriate conductors 26 to the S/H circuit 30. The voltages sensed by this circuit 30 are fed to the differential amplifier, and after amplification therein, to the scaling network 34. The scaling network generates in response on offset or error signal on line 36. The current generator 18 uses this signal to generate the current stimulation pulses as discussed below.

Figure 3A:
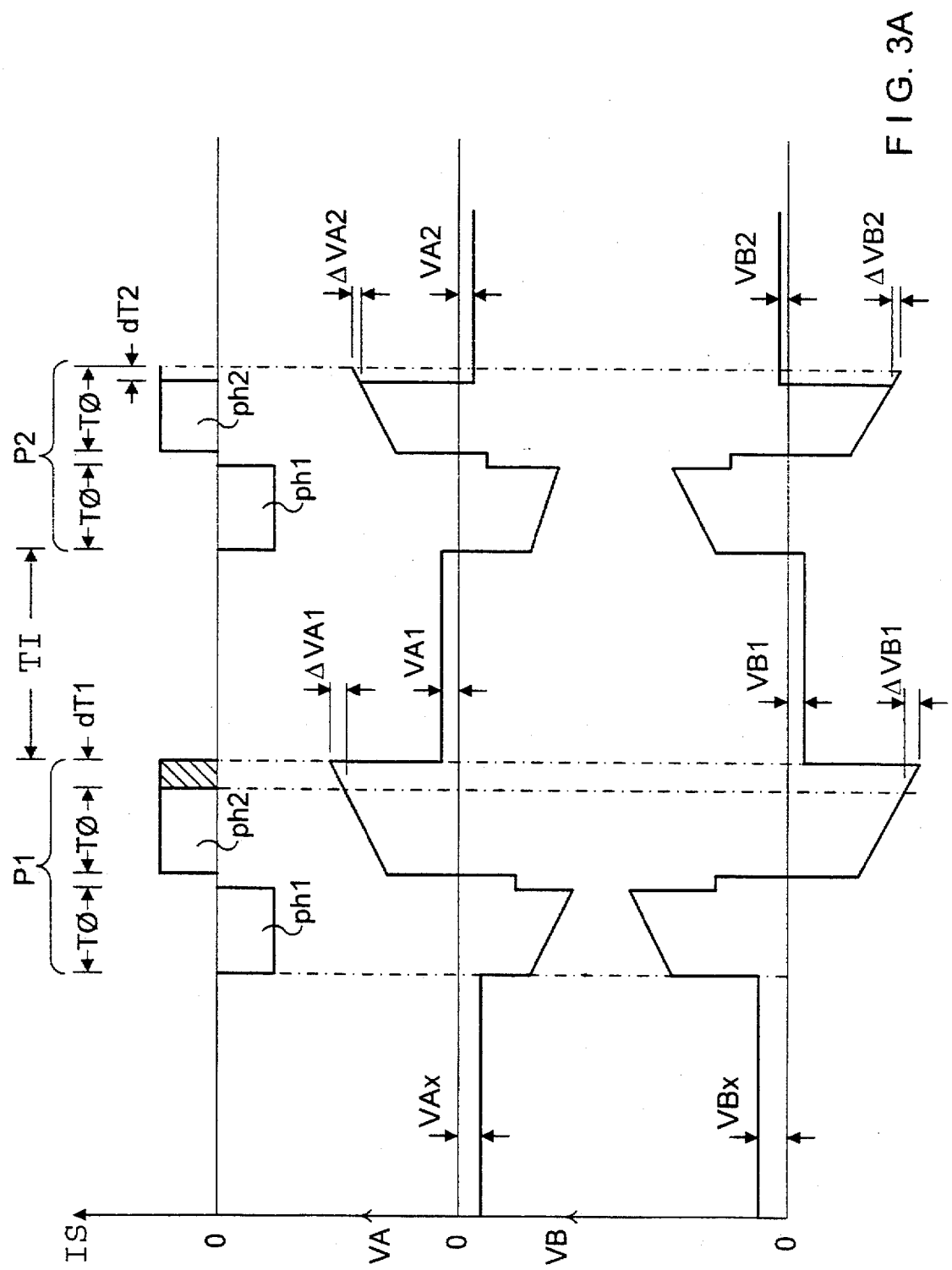
FIGS. 3A and 3B show time-dependent voltage and current pulses generated between the electrodes of FIG. 2.
Figure 3B:
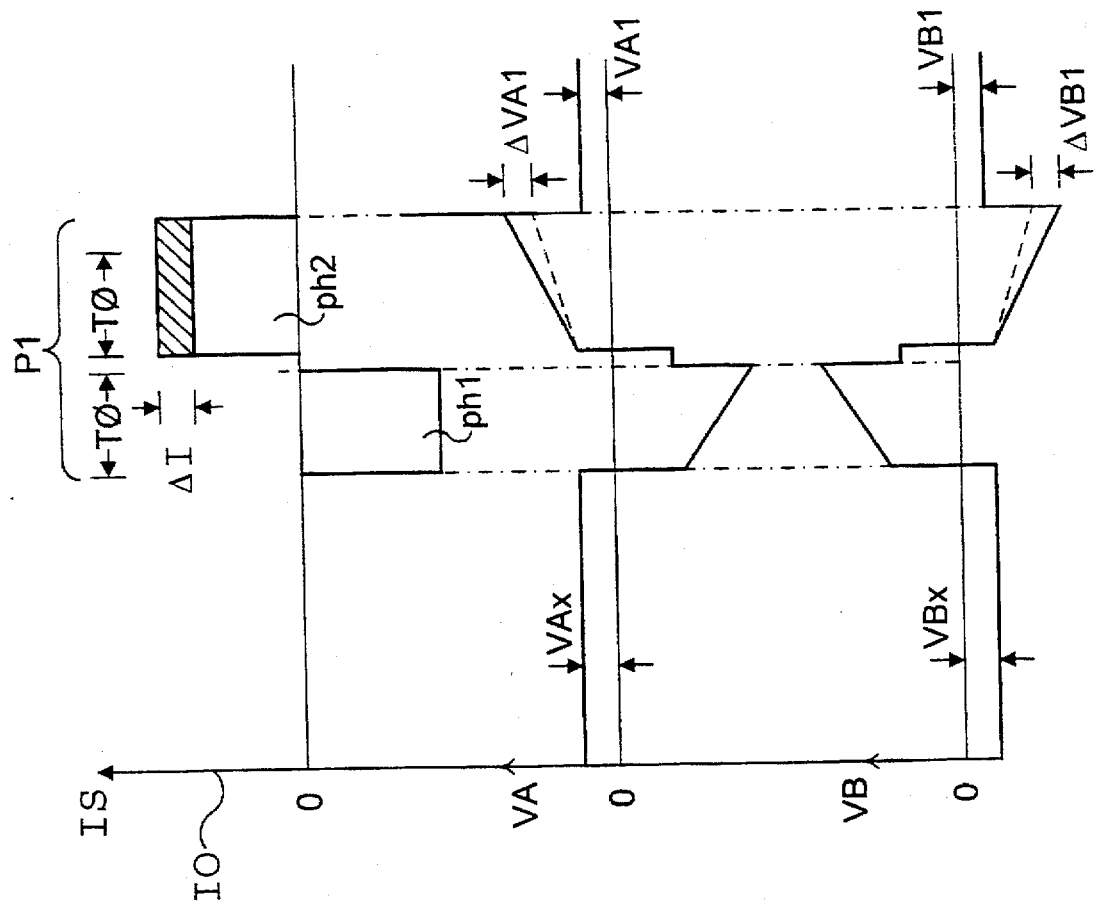

The stimulation pulses generated by the system of FIG. 1 are illustrated in FIGS. 3A and 3B. In a first embodiment of the invention shown in FIG. 3A, a biphasic current IS is applied between two electrodes 16A and 16B. This current consists of a plurality of pulses P1, P2 separated by idle periods TI. Each current pulse consists of a negative phase ph1 followed by a positive phase ph2 for substantially neutralizing residual charge or voltage build up in the tissues. The voltage between the electrode 16A and an extra-cochlear electrode such as 19 is shown as VA in FIG. 3A.

As shown in FIG. 3A, prior to pulse P1, electrode 16A is at a static residual voltage of −Vax, while the voltage on the electrode VB is Vbx. The purpose of the S/H circuit 30, amplifier 32 and scaling network 34 is to eliminate the voltage differential between electrodes 16A and 16B or alternatively to set this voltage differential to a value defined by the variable voltage offset source 31.

During the idle period, prior to pulse P1, the respective conductors 26 corresponding to electrodes 16A and 16B are connected to S/H circuit 30. This circuit measures and stores the voltages on the electrodes on capacitors 30A, 30B during the idle period prior to pulse P1, i.e., voltages −Vax and +Vbx. The voltage Vax is offset by a constant voltage offset source 31. The resulting signal and the voltage +Vbx are fed to differential amplifier which generates an output signal indicative of the difference between its inputs. This output signal is fed to a scaling network which, in response, generates a scaled feedback difference signal to the current generator 18.

The time for the onset of the next stimulation current pulse P1 is determined by the control logic 20. The current generator 18 generates the current pulses P1, P2 . . . so that their phases have a nominal duration T0. However, the current generator regulates the duration of phase ph2 in response to the signal 38 from scaling network 36 to compensate for the residual voltages on the electrodes during idle periods. For example, if the potential difference between the two electrodes 16A, 16B (i.e. Vax−VBx) is negative, then the current generator extends the duration of ph2 by an incremental amount dT1. This extended duration causes the voltage VA to rise by an amount +ΔVA1. When the pulse P1 terminates, the voltage VA drops to +VA1 as shown. Similarly the Voltage VB drops to −VB1. However, the differences between the two voltages is VA, VB, i.e., ΔVA1−ΔVB1 is smaller than it was before pulse P1. Since this difference is now positive, during the next pulse P2, the second phase ph2 is shortened by a small amount dT2. In this manner after several pulses, the residual voltages of the electrodes 16A, 16B are stabilized during the idle periods either near zero, or at a value set by the offset differential voltage source 31. The relationship between the change in the voltage in VA and VB and the amount of time dt depends on the slope of the respective voltage curves. This slope is dependent on the capacitance between the electrodes and the scabbing tissue, and since this parameter is highly variable, a deliberately small value of constant is chosen to avoid instability from positive feed back. The time required for the residual voltages to settle can therefore extend over several idle periods, as discussed above.

FIG. 3B shows a different embodiment of the invention. In this embodiment, the period of each phase ph1, ph2 remains constant (i.e., T0) for various pulses. However, their nominal amplitudes I0 is increased or decreased by ΔI by the current generator, to increase the maximum amplitudes of voltages VA, VB by ΔVA and ΔVB respectively based on the initial values VAX, VBX. The net result is that the residual electrode voltages are stabilized over several pulses, in a manner similar to the embodiment of FIG. 3A.

Figure 4:
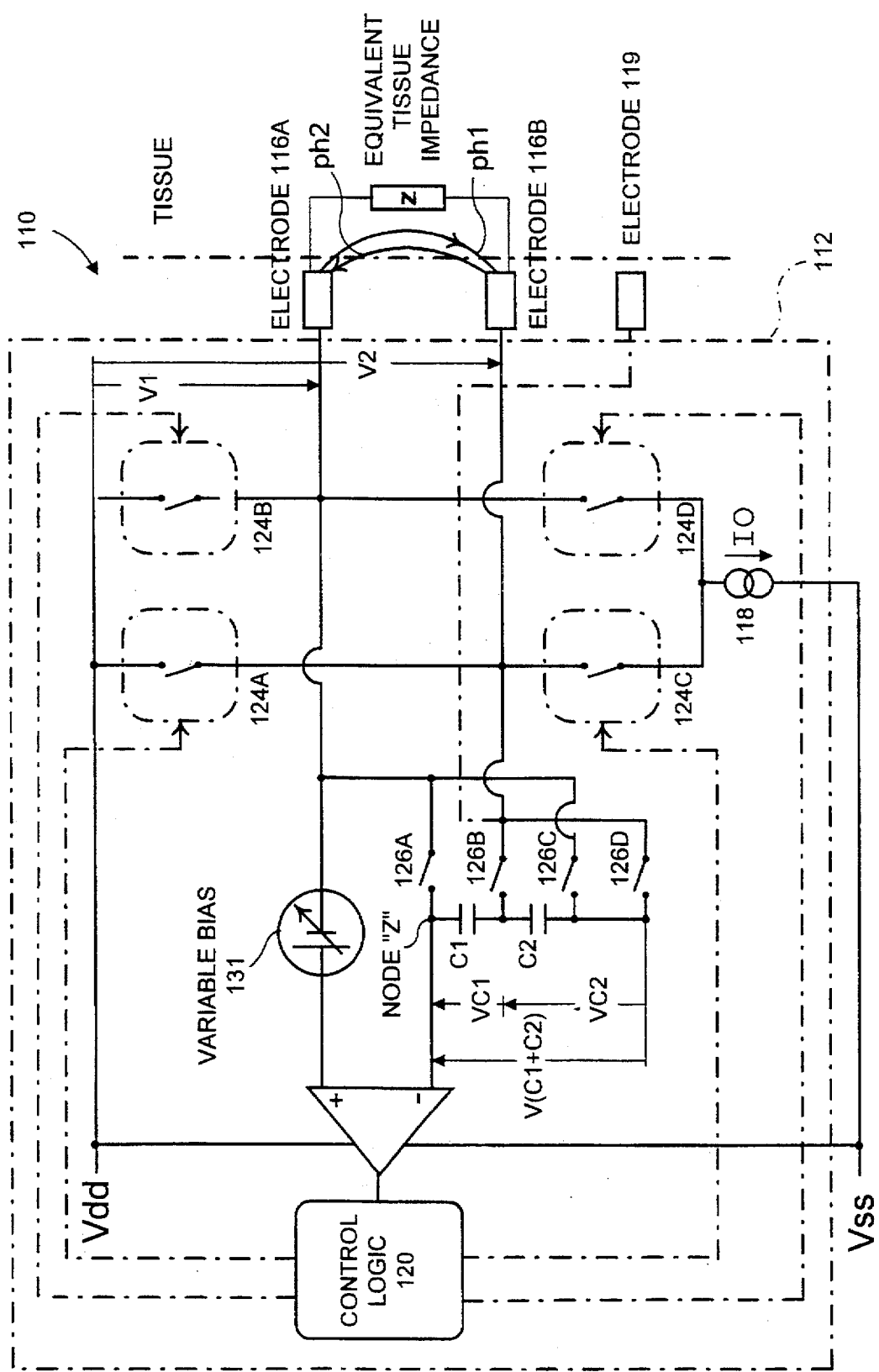
FIG. 4 shows a zero-crossing network for an alternate embodiment of the invention.
Figure 5:
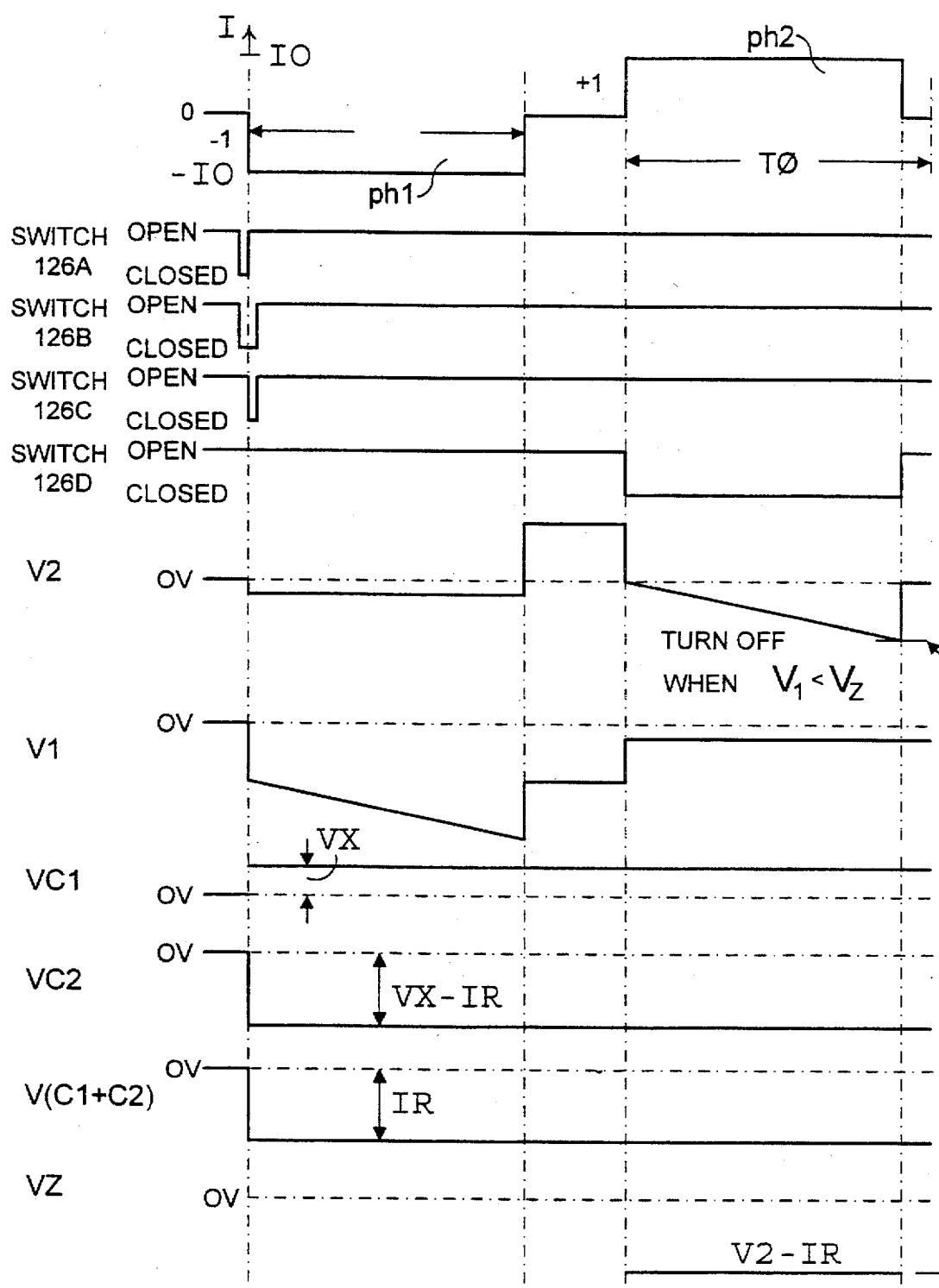
FIG. 5 shows voltage and current pulses generated in the embodiment of FIG. 4.

FIGS. 4 and 5 provide an alternate embodiment in which the relatively long time period required for the system to stabilize has been eliminated. Referring to FIG. 4, implant 110 includes a housing 112 connected to intra-cochlear electrodes 116A and 116B and an extra-cochlear electrode 119. Electrodes 116A and 116B are part of an electrode array (not shown) similar to array 16 in FIG. 1 while electrode 119 is a separate electrode similar to 19 or, alternatively, is found in housing 112.

Housing 112 includes a pair of voltage buses Vdd and Vss, a switch bridge consisting of, as an example, switches 124A, 124B, 124C and 124D and a current supply 118 generating a constant current I in the direction indicated. The housing further includes switches 126A, 126B, 126C and 126D used to monitor the voltages on the electrodes as discussed more fully below, as well as a voltage offset source 131 and a differential amplifier 132. Finally associated with switches 126A–D and amplifier 132 are two capacitors C1 and C2.

In general terms, the implant 112 applies a biphasic stimulation current pulse having two phases ph1, ph2 between electrodes 116A and 116B, similar to the phases shown in FIG. 3A. However, during ph2 the voltage on the electrodes 116A and 116B is carefully monitored and when the voltages are equal, ph2 is turned off thereby insuring that the there is no voltage drop across these electrodes. Optionally, the current phase ph2 is turned off when the voltage drop across the these electrodes reaches a preselected level. Importantly, because of the impedance Z of the tissue between the electrodes 116A, 116B, there is an IR drop during the application of the stimulation current. This IR drop is also measured and taken into consideration.

The various signals generated by the circuitry of FIG. 4 during a typical biphasic stimulation current are shown in FIG. 5. In this Figure the biphasic current pulse is shown as signal I, having phases ph1 and ph2. Next, going down from the top of the Figure, are shown the corresponding positions of switches 126A, 126B, 126C and 126D. As indicated in FIG. 4, voltage signals V1, and V2 indicate the voltages between the electrode 116A and electrode 116B and the positive bus Vdd, respectively. VC1, VC2 are the voltages across the capacitors VC1 and VC2. V(C1+C2) is the algebraic sum of the voltages across capacitors C1 and C2. Finally, voltage VZ is the voltage between node Z (the inverting input to the amplifier 132) and the bus Vdd.

The operation of the circuitry of FIG. 4 shall now be explained in conjunction with FIG. 5. All the switches 124A–D, 126A–D are controlled by control logic 120. The two phases ph1 and ph2 are generated by selective closing of switches 124A–D. More specifically, ph1 is generated by closing switches 124B and 124C, and ph2 is generated by closing 124A and 124D. While these switches are closed, current from source 118 flows between the electrodes 116A and 116B.

Switches 126A–D are used for two purposes. First, to measure the IR drop across the electrodes 116A, 116B during the application of the biphasic current pulse, and second, to provide compensation for this IR drop for the termination of ph2. More specifically, as shown in FIG. 5, switches 126A and 126B are closed for a short period just prior to ph1. During this time, there is a residual voltage VX between electrodes 116A and 116B. Closing switches 126A and 126B causes the capacitor C1 to charge to this voltage VX. When ph1 is initiated, switch 126A is opened and switch 126C is closed. During ph1 current I flows between the electrodes 116A and 116B, so that the voltage across these electrodes is VX+IR, where R represents the tissue impedance. Closing switch 126C while switch 126B is also closed causes the capacitor C2 to charge to VX–IR). The voltage reversal is caused by the manner in which the switches 126B and 126C are arranged across the capacitor C2. Because of this reversal, the net voltage across the two capacitors C1 and C2, i.e., V(C1+C2), is –IR, as shown. Shortly after ph1 is initiated, switches 126B and 126C are opened and the capacitors maintain their charge to act as a standard sample and hold circuits. Meanwhile, during ph1, the voltage V1 is slightly below Vdd (due to the voltage drop across switch 124B, since all these switches are solid state switches) and the voltage V2 has the shape of a negative ramp as shown.

At the beginning of phase ph2 switch 126D is closed. At this point amplifier 132 receives at its non-inverting input the signal V1 and the signal VZ (i.e., V2–IR) at its inverting input. Thus, during phase ph2 the amplifier compares the voltages at the electrodes 116A and 116B with automatic compensation for the IR drop therebetween. During this time, the voltage V1 drops linearly as shown in FIG. 5. This process continues until the signal V1 drops below VZ. At this moment the output of amplifier 132 forces the control logic 120 to turn switches 124A and 124D so as to end phase ph2. Thus the duration of phase ph2 can be shorter or longer than T0, the duration of phase ph1. At the end of ph2, the voltage on electrodes 116A and 116B should be the same thereby eliminating, at least theoretically any residual voltage there-between during the idle periods.

The process described above results, ideally, in no residual voltage between the electrodes. If a preselected voltage is desired between these electrodes, the offset voltage source 131 may be set for the desired voltage value. Otherwise the source 131 is set to zero.

In the embodiments shown in FIGS. 3A and 4, the voltages between the electrodes of the intra-cochlear electrodes during idle period are controlled by changing the periods of the phase ph2 of the current pulses. However these changes in duration are relatively small so that they have no effect on the ability of the patient to perceive this stimulation and to translate them into ambient sounds.

The description of the embodiment in FIG. 4 describes how the voltage between electrodes 116A and 116B, (i.e., the two electrodes through which stimulation current is passing) is controlled. An alternative arrangement is to control the voltage between electrode 116A and a third electrode 119. This is achieved by using selector switches (not shown) which connect electrode 119 rather than 116B to switches 126B and 126D at the aforementioned times. Since no current flows through electrode 119, it is therefore possible to use this electrode 119 as a stable reference voltage whose level with respect to the tissue voltage will not change. Other stimulation electrodes such as electrode 116A can therefore have the resting (idle period) level of their electrode/tissue voltage accurately controlled.

The invention can also be used to maintain zero or close to zero DC current through electrode 116A provided its electrode/tissue interface capacitance is large enough such that its voltage during a stimulation pulse is not disturbed by more than a few milli-volts. A typical extracochlear electrode easily meets this requirement. Under these circumstances the electrode/tissue interface capacitance of electrode 116A acts as a non-leaky integrator of the current passed through it. If the system is configured to maintain the voltage on electrode 116A at a constant value (by using a non-stimulated electrode 119 as a constant reference voltage) then the DC current through electrode 116A must be zero since the integrated current through it is maintained at zero by the system.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable device comprising:

pulse generating means for generating a sequence of stimulation pulses separated by idle periods, wherein said pulses have pulse periods;

a first and second electrode for receiving said stimulating pulses, with a corresponding first and second residual voltage being generated respectively intrinsically on said electrodes during said idle periods;

means for measuring a differential residual voltage corresponding to a difference between said first and second residual voltages;

means coupled to said pulse generating means, said electrodes and said means for measuring for controlling said pulses to change said differential residual voltage to a preselected value, wherein said control means adjusts said pulse periods; and a predetermined reference, wherein said measuring means measures said first and second residual voltages from each of said electrode to said predetermined reference to obtain corresponding measured voltages and wherein said control means terminates said pulse periods when said measured voltages have a preselected value.

2. The device of claim 1 wherein said preselected value is substantially zero.

3. An implantable cochlear device for applying therapeutic stimulation to a patient's cochlea with cochlear tissues, said device comprising:

a housing, including a pulse generator for generating pulses having pulse periods and being separated by idle periods;

a plurality of electrodes for receiving said pulses, each said electrode having a distal end arranged and constructed for insertion within said cochlea;

a reference point having a constant voltage with respect to said cochlear tissues;

a measuring device for measuring a corresponding residual voltage between said distal ends of said electrodes and said reference point, to obtain corresponding measured voltages, said residual voltages being generated intrinsically by electrochemical action between said distal ends and said cochlear tissues during said idle periods between said respective distal ends and said patient's cochlea;

a difference circuit for generating a differential residual voltage between said measured voltages; and a control device for selectively applying said pulses to said electrodes, said control device receiving said differential residual voltage and controlling said pulses to set said differential residual voltages to a preselected level.

4. The device of claim 3 wherein said control device includes a first set of switches for selectively connecting said pulses to said electrodes and a second set of switches for connecting said electrodes to said measuring device during said idle periods.

5. The device of claim 3 wherein said pulses are biphasic pulses.

6. The device of claim 3 wherein said control device changes said pulse periods in accordance with said measured voltages.

7. The device of claim 3 wherein said pulses have pulse amplitudes, and said control device changes said pulse amplitudes in response to said measured voltages.

8. The device of claim 3 wherein said measuring device includes a circuit for determining said residual voltages prior to each pulse to obtain initial voltages, and wherein said control device terminates each pulse after a time period dependent on said initial voltages.

9. The device of claim 3 wherein said measuring device includes a circuit for measuring an IR drop from said electrodes to said reference point during said pulses, and wherein said control device controls said pulses to adjust for said IR drop.

* * * * *